United States Patent
Li et al.

(10) Patent No.: US 9,244,015 B2
(45) Date of Patent: Jan. 26, 2016

(54) SELF-ARRANGING, LUMINESCENCE-ENHANCEMENT DEVICE FOR SURFACE-ENHANCED LUMINESCENCE

(75) Inventors: Zhiyong Li, Redwood City, CA (US); Min Hu, Sunnyvale, CA (US); Fung Suong Ou, Palo Alto, CA (US); Wei Wu, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 96 days.

(21) Appl. No.: 13/636,784

(22) PCT Filed: Apr. 20, 2010

(86) PCT No.: PCT/US2010/031809
§ 371 (c)(1),
(2), (4) Date: Sep. 24, 2012

(87) PCT Pub. No.: WO2011/133144
PCT Pub. Date: Oct. 27, 2011

(65) Prior Publication Data
US 2013/0027698 A1    Jan. 31, 2013

(51) Int. Cl.
| | |
|---|---|
| G01J 3/44 | (2006.01) |
| B05D 5/06 | (2006.01) |
| B44C 1/22 | (2006.01) |
| C23C 16/48 | (2006.01) |

(Continued)

(52) U.S. Cl.
CPC ................................... G01N 21/658 (2013.01)

(58) Field of Classification Search
USPC ............... 356/445, 300, 301, 317, 326; 435/6
See application file for complete search history.

(56) References Cited

U.S. PATENT DOCUMENTS

| | | |
|---|---|---|
| 4,901,231 A | 2/1990 | Bishop et al. |
| 5,455,953 A | 10/1995 | Russell |

(Continued)

FOREIGN PATENT DOCUMENTS

| | | |
|---|---|---|
| CN | 101688809 | 3/2010 |
| CN | 1659425 | 1/2011 |

(Continued)

OTHER PUBLICATIONS

Fan et al., "Multilayer Silver Nanoparticles Modified Optical Fiber Tip for High Performance SERS Remote Sensing," 217th ECS Meeting—Vancouver, Canada, Apr. 25-Apr. 30, 2010, J2—Electrochemical Nano/Bio Sensors 2, Abs# 1830.

(Continued)

*Primary Examiner* — Sang Nguyen
(74) *Attorney, Agent, or Firm* — HP Inc. Patent Department

(57) ABSTRACT

A self-arranging, luminescence-enhancement device 101 for surface-enhanced luminescence. The self-arranging, luminescence-enhancement device 101 for surface-enhanced luminescence includes a substrate 110, and a plurality 120 of flexible columnar structures. A flexible columnar structure 120-1 of the plurality 120 includes a flexible column 120-1A, and a metallic cap 120-1B coupled to the apex 120-1 C of the flexible column 120-1A. At least the flexible columnar structure 120-1 and a second flexible columnar structure 120-2 are configured to self-arrange into a close-packed configuration with at least one molecule 220-1 disposed between at least the metallic cap 120-1B and a second metallic cap 120-2B of respective flexible columnar structure 120-1 and second flexible columnar structure 120-2.

20 Claims, 9 Drawing Sheets

(51) Int. Cl.
  *C25D 5/02* (2006.01)
  *G02B 5/08* (2006.01)
  *G01N 21/65* (2006.01)

(56) References Cited

U.S. PATENT DOCUMENTS

| | | | |
|---|---|---|---|
| 5,513,314 A | 4/1996 | Kandasamy et al. | |
| 5,677,196 A | 10/1997 | Herron et al. | |
| 5,828,876 A | 10/1998 | Fish et al. | |
| 5,873,103 A | 2/1999 | Trede et al. | |
| 5,909,540 A | 6/1999 | Carter et al. | |
| 5,948,062 A | 9/1999 | Tzelnic et al. | |
| 5,960,446 A | 9/1999 | Schmuck et al. | |
| 5,987,506 A | 11/1999 | Carter et al. | |
| 6,023,706 A | 2/2000 | Schmuck et al. | |
| 6,163,801 A | 12/2000 | O'Donnell et al. | |
| 6,173,293 B1 | 1/2001 | Thekkath et al. | |
| 6,182,111 B1 | 1/2001 | Inohara et al. | |
| 6,185,601 B1 | 2/2001 | Wolff | |
| 6,192,408 B1 | 2/2001 | Vahalia et al. | |
| 6,193,870 B1 | 2/2001 | Morse et al. | |
| 6,222,619 B1 | 4/2001 | Herron et al. | |
| 6,324,581 B1 | 11/2001 | Xu et al. | |
| 6,330,572 B1 | 12/2001 | Sitka | |
| 6,345,244 B1 | 2/2002 | Clark | |
| 6,356,863 B1 | 3/2002 | Sayle | |
| 6,389,420 B1 | 5/2002 | Vahalia et al. | |
| 6,442,608 B1 | 8/2002 | Knight et al. | |
| 6,453,354 B1 | 9/2002 | Jiang et al. | |
| 6,516,320 B1 | 2/2003 | Odom et al. | |
| 6,571,259 B1 | 5/2003 | Zheng et al. | |
| 6,654,912 B1 | 11/2003 | Viswanathan et al. | |
| 6,756,795 B2 | 6/2004 | Hunt et al. | |
| 6,772,161 B2 | 8/2004 | Mahalingam et al. | |
| 6,777,244 B2 | 8/2004 | Pepper et al. | |
| 6,782,389 B1 | 8/2004 | Chrin et al. | |
| 6,823,336 B1 | 11/2004 | Srinivasan et al. | |
| 6,938,039 B1 | 8/2005 | Bober et al. | |
| 6,973,455 B1 | 12/2005 | Vahalia et al. | |
| 7,158,219 B2 | 1/2007 | Li et al. | |
| 7,236,242 B2 | 6/2007 | Kamins et al. | |
| 7,245,370 B2 * | 7/2007 | Bratkovski et al. | 356/301 |
| 7,256,886 B2 | 8/2007 | Cullum et al. | |
| 7,342,479 B2 | 3/2008 | Glatkowski et al. | |
| 7,342,656 B2 * | 3/2008 | Islam et al. | 356/301 |
| 7,357,906 B2 | 4/2008 | Colbert et al. | |
| 7,388,661 B2 | 6/2008 | Li et al. | |
| 7,402,531 B1 | 7/2008 | Kuekes et al. | |
| 7,463,661 B2 | 12/2008 | Ogura | |
| 7,483,130 B2 * | 1/2009 | Baumberg et al. | 356/301 |
| 7,528,948 B2 | 5/2009 | Bratkovski et al. | |
| 7,583,379 B2 | 9/2009 | Zhao et al. | |
| 7,597,814 B2 | 10/2009 | Stasiak et al. | |
| 7,656,525 B2 | 2/2010 | Zhao et al. | |
| 7,667,238 B2 | 2/2010 | Erchak | |
| 7,833,842 B2 | 11/2010 | Williams | |
| 7,898,658 B2 | 3/2011 | Moskovits et al. | |
| 7,960,251 B2 | 6/2011 | Choi et al. | |
| 8,108,943 B2 | 1/2012 | Anderson | |
| 8,148,294 B2 | 4/2012 | Wang et al. | |
| 8,149,397 B2 | 4/2012 | Lee et al. | |
| 8,154,722 B2 * | 4/2012 | Yamada et al. | 356/301 |
| 8,184,284 B2 | 5/2012 | Ebstein | |
| 8,279,435 B2 | 10/2012 | Wang et al. | |
| 8,358,408 B2 | 1/2013 | Wu et al. | |
| 2002/0059309 A1 | 5/2002 | Loy et al. | |
| 2002/0095479 A1 | 7/2002 | Schmidt | |
| 2002/0120763 A1 | 8/2002 | Miloushev et al. | |
| 2002/0138501 A1 | 9/2002 | Dake | |
| 2002/0138502 A1 | 9/2002 | Gupta | |
| 2002/0143734 A1 | 10/2002 | Loy et al. | |
| 2002/0161855 A1 | 10/2002 | Manczak et al. | |
| 2002/0180306 A1 | 12/2002 | Hunt et al. | |
| 2002/0192721 A1 | 12/2002 | Rizzuto et al. | |
| 2003/0004947 A1 | 1/2003 | Coverston | |
| 2003/0028587 A1 | 2/2003 | Driscoll et al. | |
| 2003/0033308 A1 | 2/2003 | Patel et al. | |
| 2003/0059820 A1 | 3/2003 | Vo-Dinh | |
| 2003/0077023 A1 | 4/2003 | Troll | |
| 2003/0079222 A1 | 4/2003 | Boykin et al. | |
| 2003/0110237 A1 | 6/2003 | Kitamura et al. | |
| 2003/0115434 A1 | 6/2003 | Mahalingam et al. | |
| 2003/0115438 A1 | 6/2003 | Mahalingam et al. | |
| 2004/0106203 A1 | 6/2004 | Stasiak et al. | |
| 2004/0133570 A1 | 7/2004 | Soltis | |
| 2006/0017917 A1 | 1/2006 | Cullum et al. | |
| 2006/0038990 A1 | 2/2006 | Habib et al. | |
| 2006/0119843 A1 | 6/2006 | O'Connell | |
| 2006/0119853 A1 | 6/2006 | Baumberg et al. | |
| 2006/0213259 A1 | 9/2006 | Prinz et al. | |
| 2006/0231381 A1 | 10/2006 | Jensen | |
| 2006/0252065 A1 * | 11/2006 | Zhao et al. | 435/6 |
| 2007/0020445 A1 | 1/2007 | Liu et al. | |
| 2007/0070341 A1 * | 3/2007 | Wang | 356/301 |
| 2007/0086001 A1 | 4/2007 | Islam et al. | |
| 2007/0127164 A1 | 6/2007 | Ofek et al. | |
| 2007/0132043 A1 | 6/2007 | Bradley et al. | |
| 2007/0252982 A1 * | 11/2007 | Wang et al. | 356/301 |
| 2008/0017845 A1 | 1/2008 | Drndic | |
| 2008/0024776 A1 | 1/2008 | Bratkovski et al. | |
| 2008/0080816 A1 | 4/2008 | D'Urso et al. | |
| 2008/0094621 A1 | 4/2008 | Li et al. | |
| 2008/0144026 A1 | 6/2008 | Zhao et al. | |
| 2008/0166706 A1 | 7/2008 | Xhang et al. | |
| 2008/0174775 A1 | 7/2008 | Moskovits et al. | |
| 2008/0187648 A1 | 8/2008 | Hart | |
| 2008/0311028 A1 | 12/2008 | Stanbery | |
| 2009/0084162 A1 | 4/2009 | Besnard et al. | |
| 2009/0227059 A1 | 9/2009 | Besnard et al. | |
| 2009/0261815 A1 | 10/2009 | Cairns | |
| 2009/0280593 A1 | 11/2009 | Serban et al. | |
| 2009/0303472 A1 | 12/2009 | Zhao et al. | |
| 2009/0317943 A1 | 12/2009 | Park et al. | |
| 2010/0001211 A1 | 1/2010 | Huang et al. | |
| 2010/0009338 A1 | 1/2010 | Zhang et al. | |
| 2010/0303722 A1 | 12/2010 | Jin et al. | |
| 2010/0321684 A1 * | 12/2010 | Bratkovski et al. | 356/301 |
| 2011/0001118 A1 | 1/2011 | Bhupendra | |
| 2011/0030792 A1 | 2/2011 | Miguez | |
| 2011/0128537 A1 | 6/2011 | Bond et al. | |
| 2011/0188034 A1 * | 8/2011 | Stuke et al. | 356/301 |
| 2012/0107948 A1 | 5/2012 | Li et al. | |
| 2012/0119315 A1 * | 5/2012 | Ou et al. | 257/431 |
| 2012/0188540 A1 | 7/2012 | Bratkovski et al. | |
| 2012/0212732 A1 | 8/2012 | Santori et al. | |
| 2012/0212733 A1 | 8/2012 | Kodali et al. | |
| 2013/0027698 A1 | 1/2013 | Li et al. | |
| 2013/0040862 A1 * | 2/2013 | Li et al. | 506/20 |
| 2013/0120748 A1 | 5/2013 | Li et al. | |

FOREIGN PATENT DOCUMENTS

| | | |
|---|---|---|
| CN | 101529229 | 10/2011 |
| EP | 2058908 | 5/2009 |
| EP | 1426756 | 6/2009 |
| JP | 2000-206048 | 7/2000 |
| JP | 2004-184414 | 7/2004 |
| JP | 2006145230 | 6/2006 |
| JP | 2009-515543 | 4/2009 |
| JP | 2009-544967 | 12/2009 |
| JP | 2010019688 | 1/2010 |
| KR | 20070111649 | 11/2007 |
| WO | WO-03083480 | 10/2003 |
| WO | WO-2007064355 | 6/2007 |
| WO | WO-2008013683 | 1/2008 |
| WO | WO-2008028521 | 3/2008 |
| WO | WO-2009136869 | 11/2009 |
| WO | WO-2010088585 | 8/2010 |
| WO | WO-2010126640 | 11/2010 |

(56) References Cited

FOREIGN PATENT DOCUMENTS

| WO | WO-2011133143 | 10/2011 |
|---|---|---|
| WO | WO-2011133144 | 10/2011 |

OTHER PUBLICATIONS

Fan, J. G. et al., "Integrating Aligned Nanorod Array onto Optical Fibers for SERS Probes," Proc. of SPIE—Nanoengineering: Fabrication, Properties, Optics, and Devices III, vol. 6327, 2006, pp. R-1 to R10.

Guieu, Valérie, et al. "Multitip-localized enhanced Raman scattering from a nanostructured optical fiber array." The Journal of Physical Chemistry C 113.3 (2008): 874-881.

International Search Report, Mar. 30, 2011, PCT Application No. PCT/US2010/044039, Filed Jul. 30, 2010.

Lucotti et al., "Fiber-optic SERS sensor with optimized geometry," Elsevier, ScienceDirect, Sensors and Actuators B, vol. 121, 2007, 356-364.

Ren, Hongliang, et al. "The preparation of optical fibre nanoprobe and its application in spectral detection." Optics & Laser Technology 39.5 (2007): 1025-1029.

White, Daniel J., et al. "Nanostructured optical fibre for surface-enhanced Raman scattering sensing." Proc SPIE. vol. 7102. 2008.

Xie et al., "Polymer optical fiber SERS sensor with gold nanorods," Elsevier, Optics Communications, vol. 282, 2009, pp. 439-442.

Zhang et al., "Single-Fiber Probe Based on Surface Enhanced Raman Scattering (SERS)," IEEE Sensors, 2005, pp. 1088-1091.

Baldwin, Jean, Norbert Schuhler, Ian S. Butler, & Mark P. aNDREWS, "Integrated Optics Evanescent Wave Surface Enhanced Raman Scattering (IO-EWSERS) of Mercaptopyridines on a Planar Optical Chemical Bench: Binding of Hydrogen and Copper Ion", Langmuir, 1996, vol. 12, pp. 6389-6398.

Chen, S.Y. et al., Raman Antenna Formed by Molecule/plasmonic Nanostructure Hybrid System, (Research Paper), Conference Paper, Quantum Electronics and Laser Science Conference, May 1, 2011, Baltimore, Maryland.

Du, Y. et al., SERSEnhancement1 Dependence on the Diameter and Aspect Ratio of Silver-nanowire Array Fabricated by Anodic Aluminium Oxide Template, (Research Paper), Applied Surface Science, Dec. 30, 2008, pp. 1901-1905, vol. 255, No. 5.

Gopinath, Ashwin, et al., Deterministic Aperiodic Arrays of Metal Nanoparticles for Surface-enhanced Raman Scattering (SERS), Publication Date: Mar. 2, 2009; vol. 17; On pp. 3741-3753. <http://www.bio-page.org/boriskina/Boriskina_OE2009.pdf>.

Josef Giglmayr, "Nano-Finger Electrodes for the Electro-Optical Generation and Tuning of Gratings at Several Wavelengths", <http://www.ipme.ru/ipme/conf/NN2003/NN2003_Abstracts.pdf> Publication Date: Aug. 30, 2003-Sep. 6, 2003.

Krishnamoorthy, Sivashankar, et al., Combining Micelle Self-assembly with Nanostencil Lithography to Create Periodic/aperiodic Micro-/nanopatterns on Surfaces, Publication Date: Jul. 30, 2008; vol. 20; on pp. 3533-3538. < http://onlinelibrary.wiley.com/doi/10.1002/adma.200702478/abstract >.

Weng, T.W. et al., Area Effect of Patterned Carbon Nanotube Bundle on Field Electron Emission Characteristics, (Research Paper), 9th International Conference on Atomically Controlled Surfaces, Interfaces and Nanostructures 2007, Sep. 30, 2008, pp. 7755-7758, vol. 254, No. 23.

Cubukcu, E., et al., "Plasmonic Laser Antennas and Related Devices", IEEE Journal of Selected Topics in Quantum Electronics, Nov./Dec. 2008, vol. 14, No. 6, pp. 148-1461.

PCT International Search Report, Jan. 20, 2011, Hewlett-Packard Development Company, L.P. (PCT/US2010/031790, Filed Apr. 20, 2010).

PCT International Search Report, Dec. 23, 2010, Hewlett-Packard development Company, L.P. (PCT/US2010/031809, Filed Apr. 20, 2010).

Segawa, H., et al., "Top-gathering pillar array of hybrid organic-inorganic material by means of self-organization", Applied Physics A—Materials Science & Processing, Mar. 17, 2006, vol. 83, pp. 447-451.

\* cited by examiner

600A

SELF-ARRANGING, LUMINESCENCE-ENHANCEMENT DEVICE FOR SURFACE-ENHANCED LUMINESCENCE

STATEMENT OF GOVERNMENT INTEREST

This invention was made with government support under Contract No. HR0011-09-3-0002, awarded by Defense Advanced Research Projects Agency. The government has certain rights in the invention.

RELATED APPLICATIONS

This Application is related to U.S. patent application, Ser. No. PCT/US2010/031790 by Zhiyong Li et al., filed on Apr. 20, 2010, entitled "MULTI-PILLAR STRUCTURE FOR MOLECULAR ANALYSIS," and assigned to the assignee of the present invention.

TECHNICAL HELD

Embodiments of the present invention relate generally to devices for surface-enhanced luminescence.

BACKGROUND

Surface-enhanced luminescence techniques, such as surface-enhanced Raman spectroscopy (SERS), have emerged as leading-edge techniques for the analysis of the structure of inorganic materials and complex organic molecules. For example, in SERS, scientists engaged in the application of Raman spectroscopy have found that by decorating a surface, upon which a molecule is later adsorbed, with a thin layer of a metal in which surface plasmons have frequencies in a range of electromagnetic radiation used to excite such a molecule and in which surface plasmons have frequencies in a range of electromagnetic radiation emitted by such a molecule, it is possible to enhance the intensity of a Raman spectrum of such a molecule.

In addition, spectroscopists utilizing spectroscopic techniques for the analysis of molecular structures have a continuing interest in improving the sensitivity of their spectroscopic techniques. Not only is improved sensitivity desirable for reducing the time of analysis, but also improved sensitivity can provide previously unachievable results. For example, improved sensitivity is directly related to lower detectability limits for previously undetected molecular constituents. Thus, scientists engaged in the application of surface-enhanced luminescence techniques are motivated to improve the sensitivity of surface-enhanced luminescence techniques, for example, SERS, for the detection of molecules and the spectral signatures of moieties in these molecules.

DESCRIPTION OF THE DRAWINGS

The accompanying drawings, which are incorporated in and form a part of this specification, illustrate embodiments of the invention and, together with the description, serve to explain the embodiments of the invention.

Figure 1:
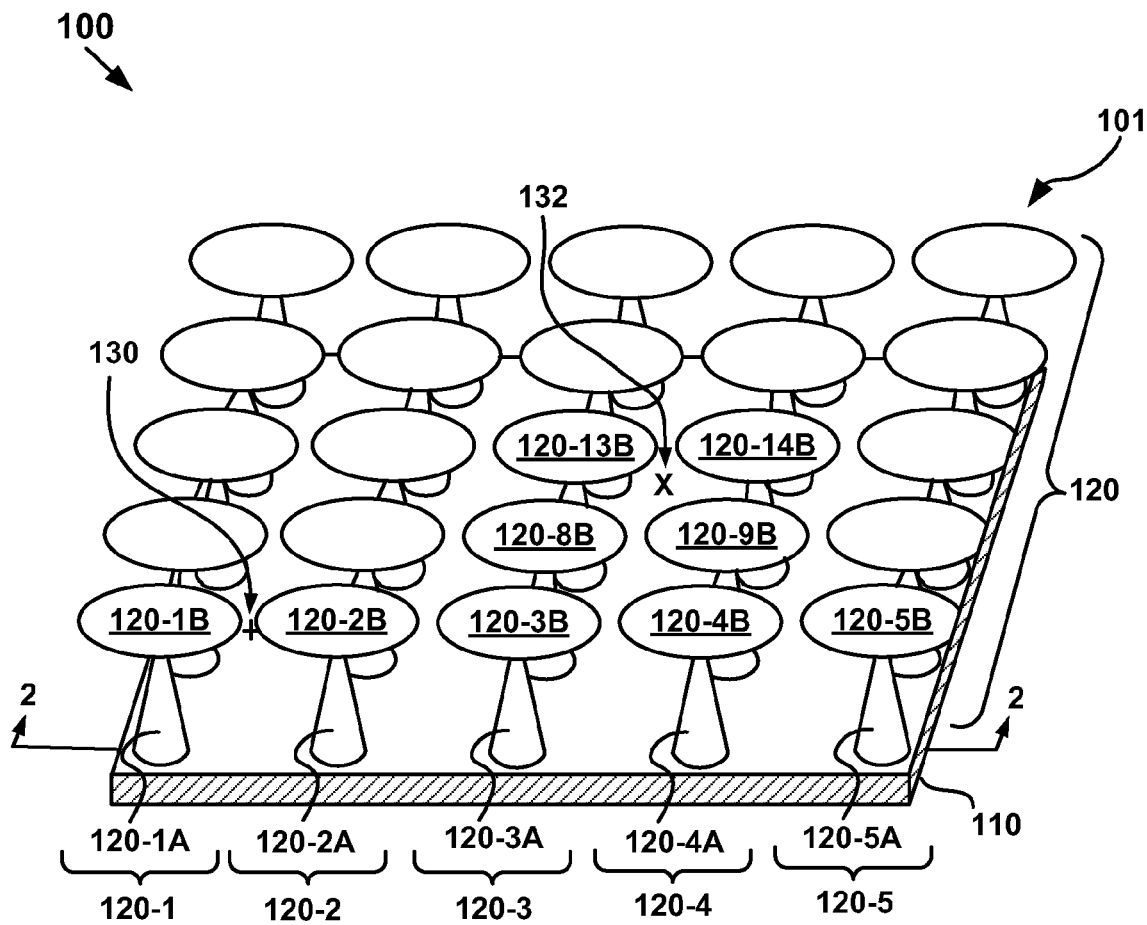
FIG. 1 is a perspective view of a self-arranging, luminescence-enhancement device, in accordance with embodiments of the present invention.

The drawings referred to in this description should not be understood as being drawn to scale except if specifically noted.

DESCRIPTION OF EMBODIMENTS

Reference will now be made in detail to the alternative embodiments of the present invention. While the invention will be described in conjunction with the alternative embodiments, it will be understood that they are not intended to limit the invention to these embodiments. On the contrary, the invention is intended to cover alternatives, modifications and equivalents, which may be included within the spirit and scope of the invention as defined by the appended claims.

Furthermore, in the following description of embodiments of the present invention, numerous specific details are set forth in order to provide a thorough understanding of the present invention. However, it should be noted that embodiments of the present invention may be practiced without these specific details. In other instances, well known methods, procedures, and components have not been described in detail as not to unnecessarily obscure embodiments of the present invention. Throughout the drawings, like components are denoted by like reference numerals, and repetitive descriptions are omitted for clarity of explanation if not necessary.

Embodiments of the present invention include a self-arranging, luminescence-enhancement device for surface-enhanced luminescence. The self-arranging, luminescence-enhancement device for surface-enhanced luminescence includes a substrate, and a plurality of flexible columnar structures. A flexible columnar structure of the plurality includes a flexible column, and a metallic cap coupled to the apex of the flexible column. At least the flexible columnar structure and a second flexible columnar structure are configured to self-arrange into a close-packed configuration with at least one molecule disposed between at least the metallic cap and a second metallic cap of the respective flexible columnar structure and the second flexible columnar structure.

With reference now to FIG. 1, in accordance with embodiments of the present invention, a perspective view 100 is shown of a self-arranging, luminescence-enhancement device 101. The self-arranging, luminescence-enhancement device 101 for surface-enhanced luminescence includes a substrate 110, and a plurality 120 of flexible columnar structures, for example, flexible columnar structures 120-1, 120-2, 120-3, 120-4 and 120-5. A flexible columnar structure 120-1 of the plurality 120 includes a flexible column 120-1A, and a metallic cap 120-1B. Similarly, other flexible columnar structures, for example, flexible columnar structures 120-2, 120-3, 120-4 and 120-5, of the plurality 120 include flexible columns, for example, flexible columns 120-2A, 120-3A, 120-4A and 120-5A, respectively, and metallic caps, for example, metallic caps 120-2B, 120-33, 120-4B and 120-5B, respectively. As shown in FIG. 1, by way of example, a row of flexible columnar structures includes flexible columnar structures 120-1, 120-2, 120-3, 120-4 and 120-5, without limitation thereto; and, by way of example, an array of flexible columnar structures includes several rows, without limitation thereto. Thus, in accordance with one embodiment of the present invention, the plurality 120 of flexible columnar structures includes the array of flexible columnar structures including several rows of flexible columnar structures. However, other arrangements of flexible columnar structures that are less well-ordered than shown in FIG. 1 are also within the spirit and scope of embodiments of the present invention. The arrangement shown in FIG. 1 is illustrative of but one example of an arrangement of the plurality 120 of flexible columnar structures in a self-arranging, luminescence-enhancement device 101 as may be fabricated in a top-down fabrication procedure, which employs a reticulated mask in a photolithographic process; but, other methods of fabrication are also within the spirit and scope of embodiments of the present invention, which are subsequently described.

Figure 4:
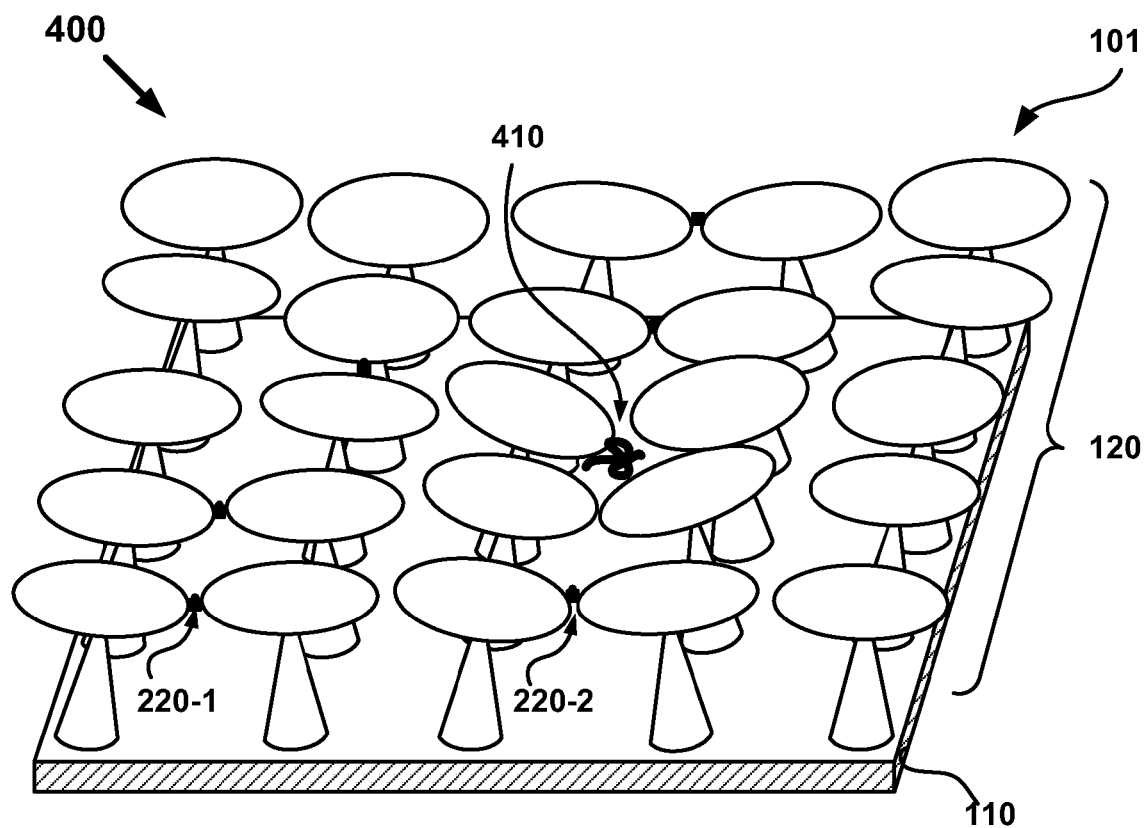
FIG. 4 is another perspective view of the self-arranging, luminescence-enhancement device of FIG. 1 after the flexible columnar structures have self-arranged into close-packed configurations with molecules disposed between the metallic caps, in accordance with embodiments of the present invention.

With further reference to FIG. 1, in accordance with embodiments of the present invention, a flexible columnar structure, for example, flexible columnar structure 120-1, of the plurality 120 of flexible columnar structures may have the shape of a mushroom, so that the inventors have coined the figurative term, "mushroom structure," for the flexible columnar structure. However, in accordance with embodiments of the present invention, a flexible columnar structure is not limited to having the shape of a mushroom, as other shapes are also within the spirit and scope of embodiments of the present invention. Moreover, by way of example, in accordance with embodiments of the present invention, the flexible columns may have the form of nanocones, as shown in FIGS. and 4, without limitation thereto; but, more generally, the flexible columns may be selected from the group consisting of: nanocones, nanopyramids, nanorods, nanobars, nanopoles and nanograss, without limitation thereto. As used herein, the terms of art, "nanocones, nanopyramids, nanorods, nanobars, nanopoles and nanograss," refer to structures that are substantially: conical, pyramidal, rod-like, bar-like, pole-like and grass-like, respectively, which have nano-dimensions as small as a few tens of nanometers (nm) in height and a few nanometers in diameter, or width. For example, flexible columns may include nano-columns having the following dimensions: a diameter of 50 nm to 500 nm, a height of 50 nm to 2 micrometers (μm), and a gap between flexible columns of 20 nm to 500 nm. The terms of art, substantially conical, substantially pyramidal, substantially rod-like, substantially bar-like, substantially pole-like and substantially grass-like, means that the structures have nearly the respective shapes of cones, pyramids, rods, bars, poles and grass-like asperities within the limits of fabrication with nanotechnology. Furthermore, by way of example, in accordance with embodiments of the present invention, the metallic caps may have the form of oblate nanospheroids, as shown in FIGS. 1 and 4, without limitation thereto; but, more generally, the metallic caps may be selected from the group consisting of: nanospheres, prolate nanospheroids, oblate nanospheroids, nanodisks, and nanoplates, without limitation thereto. As used herein, the terms of art, "nanospheres, prolate nanospheroids, oblate nanospheroids, nanodisks, and nanoplates," refer to structures that are substantially: spherical, prolate spheroidal, oblate spheroidal, disk-like, and plate-like, respectively, which have nano-dimensions as small as a few nanometers in size: height, diameter, or width. For example, in accordance with embodiments of the present invention, the diameter of the metallic caps is on the order of 20 nm to 500 nm. In addition, the terms of art, substantially spherical, substantially prolate spheroidal, substantially oblate spheroidal, substantially disk-like, and substantially and plate-like, means that the structures have nearly the respective shapes of spheres, prolate spheroids, oblate spheroids, disks, and plates within the limits of fabrication with nanotechnology.

With further reference to FIG. 1, in accordance with embodiments of the present invention, the metallic cap 120-1B is coupled to an apex 120-1C (not shown in FIG. 1, but see FIGS. 6B and 6C) of the flexible column 120-1A. Similarly, other metallic caps, for example, metallic caps 120-2B, 120-3B, 120-4B and 120-5B, are coupled to apices, for example, apices 120-2C, 120-3C, 120-4C and 120-5C, respectively, (not shown in FIG. 1, but see FIGS. 6B and 6C) of flexible columns, for example, flexible columns 120-2A, 120-3A, 120-4A and 120-5A, respectively. As shown in FIG. 1, a plurality of interstices is disposed between the plurality 120 of flexible columnar structures. For example, a small interstice 130 is located between metallic cap 120-1B and metallic cap 120-2B. By way of further example, an interstice of a different kind, a large interstice 132, is located between four metallic caps 120-8B, 120-9B, 120-13B and 120-14B. Such interstices are configured to receive molecules (not shown, but see FIG, 2) for the purpose of surface-enhanced luminescence. As used herein, the term of art, "surface-enhanced luminescence," also embraces within the scope of its meaning surface-enhanced Raman emission, as in surface-enhanced Raman spectroscopy (SERS), and surface-enhanced fluorescence. In accordance with embodiments of the present invention, at least the flexible columnar structure 120-1 and a second flexible columnar structure 120-2 of the plurality 120 are configured to self-arrange into a close-packed configuration with at least one molecule 220-1 (not shown, but see FIG. 2) disposed between at least the metallic cap 120-1 B and a second metallic cap 120-2B of respective flexible columnar structure 120-1 and second flexible columnar structure 120-2, for example, at the location of the small interstice 130, as is next described with the aid of a cross-section through line 2-2.

Figure 2:
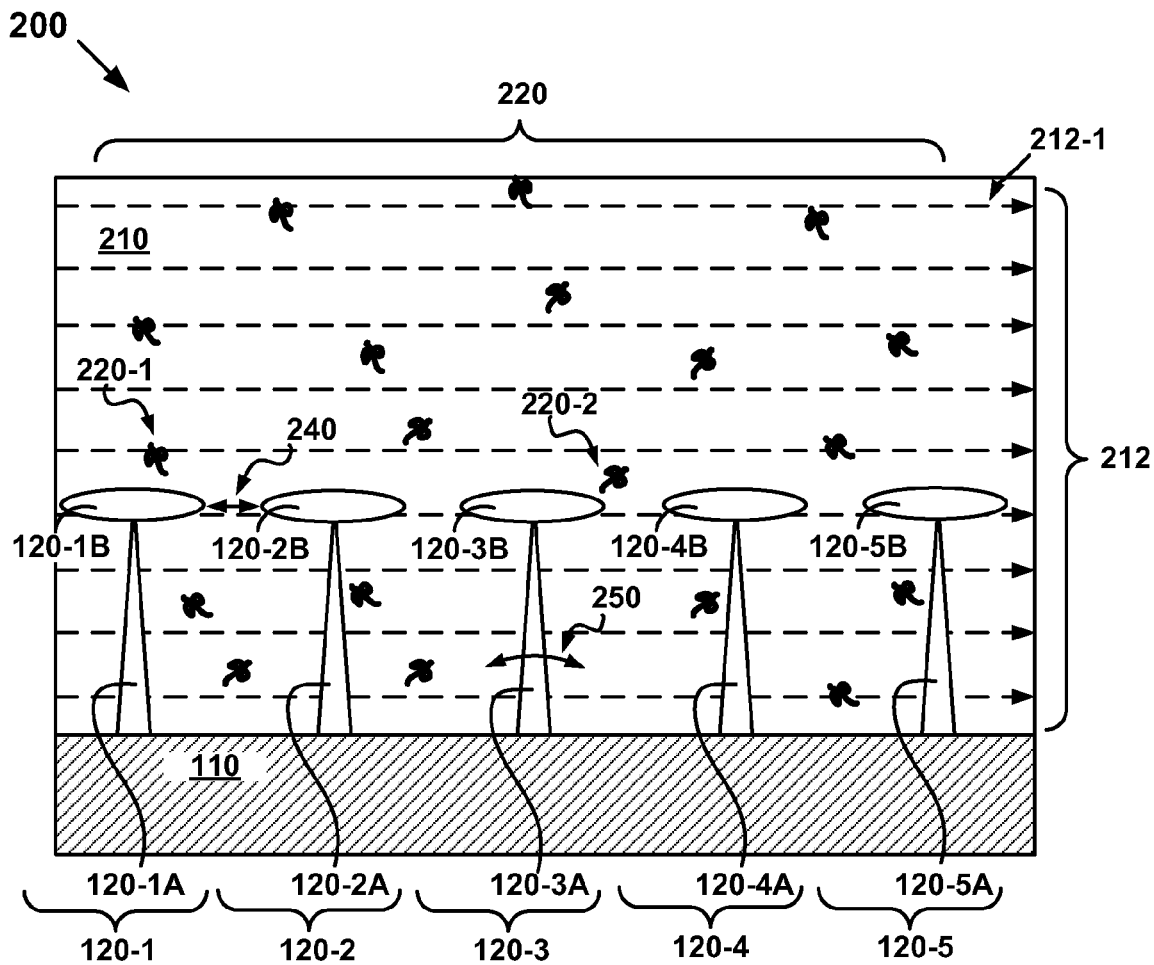
FIG. 2 is a cross-sectional elevation view, through line 2-2 of FIG. 1, of the self-arranging, luminescence-enhancement device in contact with a fluid carrier carrying a plurality of molecules, in accordance with embodiments of the present invention.

With reference now to FIG. 2, in accordance with embodiments of the present invention, a cross-sectional elevation view 200 is shown of the self-arranging, luminescence-enhancement device 101 through line 2-2 of FIG. 1. FIG. 2 shows a row of flexible columnar structures 120-1, 120-2, 120-3, 120-4 and 120-5 in profile; flexible columnar structures 120-1, 120-2, 120-3, 120-4 and 120-5 include flexible columns 120-1A, 120-2A, 120-3A, 120-4A and 120-5A, and metallic caps 120-1B, 120-2B, 120-3B, 120-4B and 120-5B, respectively. As shown in FIG. 2, the range of flexibility of each of the flexible columns 120-1A, 120-2A, 120-3A, 120-4A and 120-5A is indicated by the example double headed arrow 250, which is shown overlaying flexible column 120-3A, As further shown in FIG. 2, the row of flexible columnar structures 120-1, 120-2, 120-3, 120-4 and 120-5 of the self-arranging, luminescence-enhancement device 101 is configured to come into contact with a fluid carrier 212 carrying a plurality 220 of molecules, for example, molecules 220-1 and 220-2. By way of example, as shown in FIG. 2, the fluid carrier may be in motion, without limitation thereto, as indicated by flow vectors, of which flow vector 212-1 is an example; such a configuration might be suitable for sampling an environment with the self-arranging, luminescence-enhancement device 101 for the presence of a suspect molecule. Alternatively, the fluid carrier may be static without motion, as might be the case for immersion of the self-arranging, luminescence-enhancement device 101 in a solution containing an analyte including the fluid carrier and molecules of which the analyte is composed. In accordance with embodiments of the present invention, the term of art, "fluid," is used in a general sense so that the fluid may be a liquid, or alternatively, a gas. Thus, the self-arranging, luminescence-enhancement device 101 is configured to receive molecules of an analyte for spectroscopic analysis as is SERS, surface-enhanced fluorescence spectroscopy, or other surface-enhanced luminescence applications.

With further reference to FIG. 2, in accordance with embodiments of the present invention, an analyte molecule 220-1 may approach the site of an interstice, for example, interstice 130, where adjacent metallic caps, for example, metallic caps 120-1B and 120-2B, are separated by a distance 240. In accordance with an embodiment of the present invention, a metallic cap, for example, metallic cap 120-1 B, of the plurality 120 of flexible columnar structures is configured to bind to a molecule 220-1 disposed in close proximity to the metallic cap 120-1B. By way of example, such binding may occur through Van der Waals forces between the metallic cap 120-1 B and the molecule 220-1, without limitation thereto; or alternatively, such binding may occur through other types of binding forces, such as surface physisorption or surface chemisorption of the molecule by the metallic cap 120-1B, without limitation thereto. Once the molecule is bound to a metallic cap, for example, metallic cap 120-1 B, in accordance with an embodiment of the present invention, at least one metallic cap, for example, metallic cap 120-1 B, of a plurality 630 (see FIG. 6C) of metallic caps is configured to enhance luminescence from the molecule 220-1 disposed in close proximity to the metallic cap 120-1B. Moreover, in accordance with another embodiment of the present invention, at least one metallic cap, for example, metallic cap 120-1B, of the plurality 630 (see FIG. 60) of metallic caps may be composed of a constituent that enhances surface luminescence, such as a material selected from the group consisting of copper, silver, aluminum and gold, or any combination of copper, silver, aluminum and gold. Furthermore, in accordance with another embodiment of the present invention, the flexible columns 120-1A, 120-2A, 120-3A, 120-4A and 120-5A of the plurality 120 of flexible columnar structures 120-1, 120-2, 120-3, 120-4 and 120-5 further include a flexible material selected from the group, which includes both dielectric and non-dielectric materials, consisting of a highly cross-linked uv-curable or thermal-curable polymer, a highly cross-linked uv-curable or thermal-curable plastic, a polysiloxane compound, silicon, silicon dioxide, spin-on glass, a sol-gel material, silicon nitride, diamond, diamond-like carbon, aluminum oxide, sapphire, zinc oxide, and titanium dioxide, the purpose of which is next described.

Figure 3:
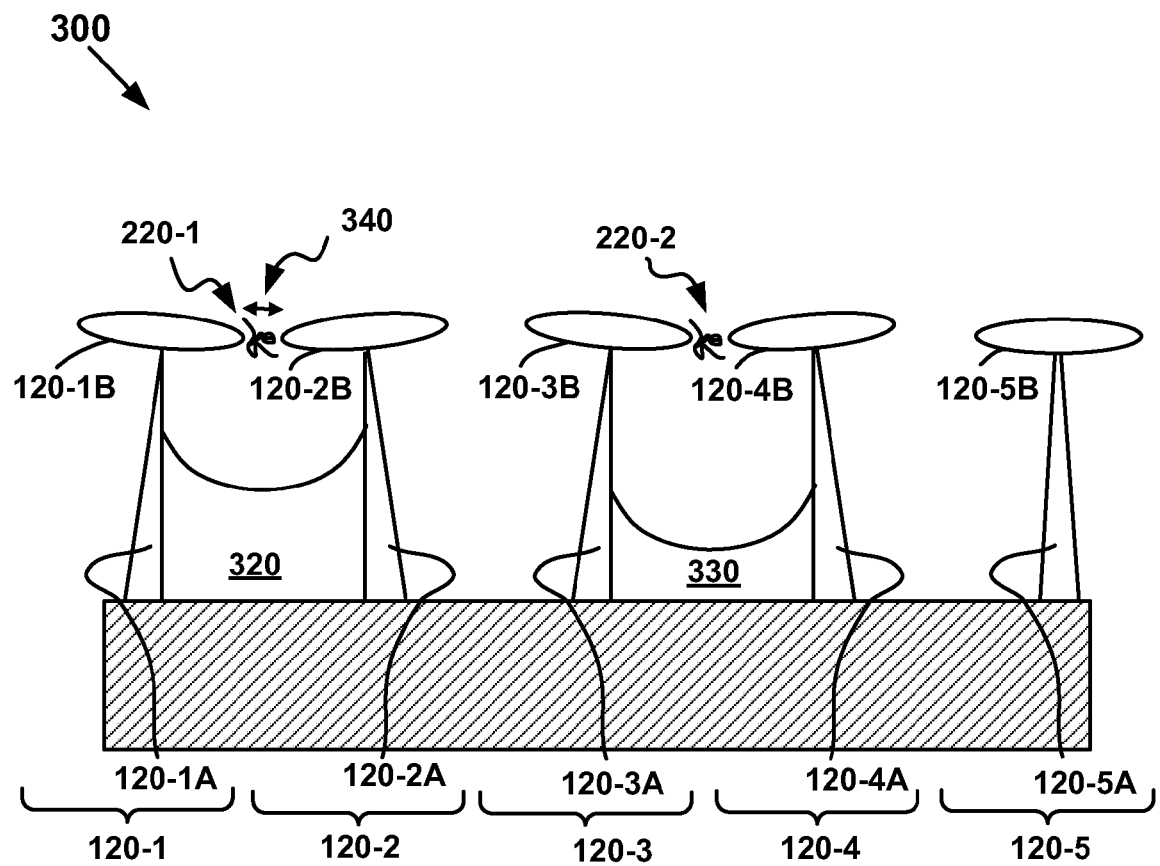
FIG. 3 is a cross-sectional elevation view through line 2-2 of FIG. 1 of the self-arranging, luminescence-enhancement device that shows flexible columnar structures self-arranging into close-packed configurations with molecules disposed between metallic caps of flexible columnar structures, in accordance with embodiments of the present invention.

With reference now to FIG. 3, in accordance with embodiments of the present invention, a cross-sectional elevation view 300 is shown of the self-arranging, luminescence-enhancement device 101 through line 2-2 of FIG. 1. FIG. 3 shows flexible columnar structures 120-1, 120-2, 120-3 and 120-4 self-arranging into close-packed configurations with molecules, for example, molecule 220-1, disposed between metallic caps 120-1B and 120-2B of the flexible columnar structures 120-1 and 120-2, respectively, and molecule 220-2, disposed between metallic caps 120-3B and 120-43 of the flexible columnar structures 120-3 and 120-4, respectively. Because the flexible columns 120-1A, 120-2A, 120-3A and 120-4A of the plurality 120 of flexible columnar structures include a flexible, or compliant, material as described above, in accordance with an embodiment of the present invention, at least one flexible column 120-1A is configured to bend towards at least a second flexible column 120-2A, and to dispose the molecule 220-1 in close proximity with at least a second metallic cap 120-2B on the second flexible column 120-2A. In the case where the fluid carrier includes a liquid, small amounts of liquid, for example, liquid pools 320 and 330, may remain trapped between the flexible columns, for example, flexible columns 120-1A and 120-2A, and flexible columns 120-3A and 120-4A, respectively, which give rise to microcapillary forces exerted upon the flexible columns; the microcapillary forces serve to draw together the flexible columns, for example, flexible columns 120-1A and 120-2A, and flexible columns 120-3A and 120-4A, as the liquid evaporates, which allows the flexible columnar structures 120-1 and 120-2 to self-arrange into a close-packed configuration with at least one molecule 220-1 disposed between at least the metallic cap 120-1 B and a second metallic cap 120-2B of respective flexible columnar structure 120-1 and second flexible columnar structure 120-2.

Thus, with further reference to FIG. 3, in the case where the fluid carrier includes a liquid, in accordance with embodiments of the present invention, the flexible column 120-1A is configured to bend towards the second flexible column 120-2A under action of microcapillary forces induced by removal of the fluid carrier 210, a liquid, provided to carry the molecule 220-1 into proximity with the metallic cap 120-1B and second metallic cap 120-2B. In accordance with another embodiment of the present invention, a spacing 340 of the dose-packed configuration between the metallic cap 120-1B and second metallic cap 120-2B with a molecule 220-1 disposed between the metallic cap 120-1 B and second metallic cap 120-2B is determined by a balance of binding forces, between the molecule 220-1 and the metallic cap 120-13 and second metallic cap 120-2B, with restoring forces exerted by the flexible column 120-1A and second flexible column 120-2A due to displacement of the flexible column 120-1A and second flexible column 120-2A towards the molecule 220-1. Thus, in accordance with an embodiment of the present invention, the spacing 340 approaches a limit determined by the size of the molecule 220-1, which may be as small as 0.5 nm; the spacing 340 approaches the physical limit of the smallest possible separation between metallic caps 120-1B and 120-2B; and, thus, the metallic caps act as two antennas approaching the largest coupling that may be possible between at least two such antennas for surface-enhanced luminescence. Moreover, the effect of coupling more than two antennas is also within the spirit and scope embodiments of the present invention, which is next described.

With reference now to FIG. 4 and further reference to FIGS. 1 and 3; in accordance with embodiments of the present invention, another perspective view 400 is shown of the self-arranging; luminescence-enhancement device 101 of FIG. 1. As shown in FIG. 4, most of the flexible columnar structures of the plurality 120 have self-arranged into close-packed configurations with molecules, for example, molecules 220-1, 220-2 and 410, disposed between the metallic caps, for example, metallic caps 120-1 B and 120-2B, metallic caps 120-3B and 120-4B, and metallic caps 120-8B, 120-9B, 120-13B and 120-14B, respectively. In accordance with embodiments of the present invention, the corresponding flexible columns coupled with the metallic caps have bent towards adjacent flexible columns, as might occur under action of microcapillary forces induced by removal of the fluid carrier 210, which in this case is a liquid. For example, the small interstices, similar to interstice 130, are configured to capture smaller molecules, for example, molecules 220-1 and 220-2; and, the large interstices, similar to interstice 132, are configured to capture larger molecules, for example, molecule 410. In accordance with embodiments of the present invention, the size of the molecules captured is determined by the self-arranging spacing between the metallic caps, for example, the spacing 340 of the close-packed configuration between the metallic cap 120-1B and second metallic cap 120-2B with the molecule 220-1 disposed between the metallic cap 120-1 B and second metallic cap 120-2B. By way of example, in accordance with embodiments of the present invention, the size of the self-arranging spacing may be on the order of 2 nm, without limitation thereto. Thus, in accordance with embodiments of the present invention, the self-arranging, luminescence-enhancement device 101 may be configured to provide a substrate for the capture of molecules of various sizes from a solution carrying an analyte of at least one particular molecular species. For example, the self-arranging, luminescence-enhancement device 101 may then be used in SERS analysis of the captured molecules of an analyte, which is next described in greater detail.

Figure 5:
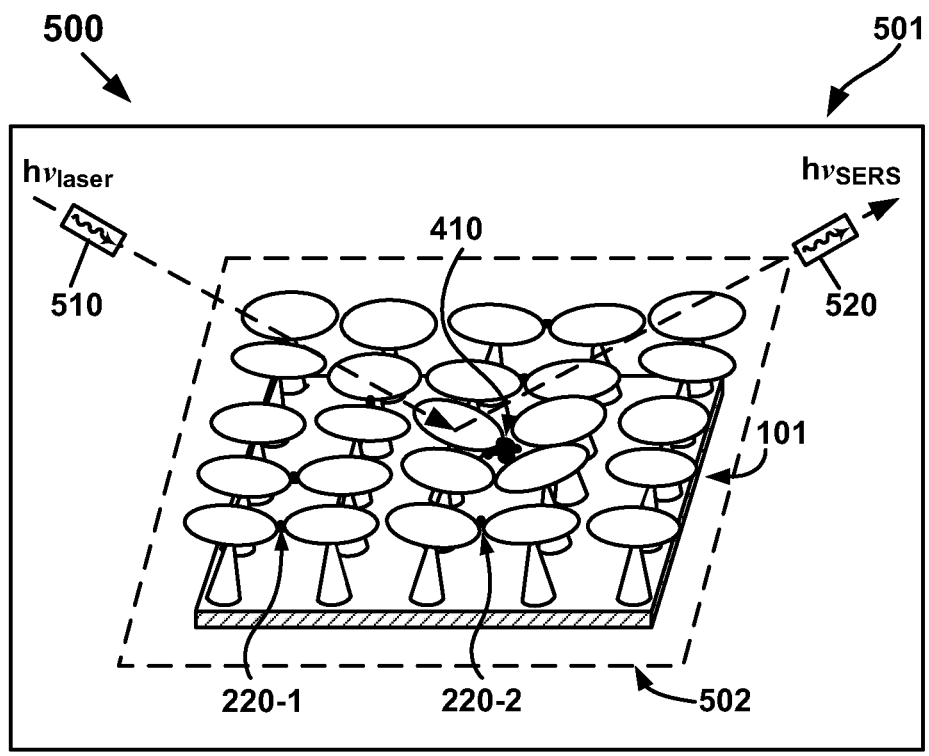
FIG. 5 is a schematic diagram of an optical apparatus including an optical component that includes the self-arranging, luminescence-enhancement device for surface-enhanced luminescence of FIG. 1, which shows an example configuration for surface-enhanced Raman spectroscopy (SERS) of molecules disposed between the metallic caps, in accordance with embodiments of the present invention.

With reference now to FIG. 5 and further reference to FIGS. 1, 3 and 4, in accordance with other embodiments of the present invention, a schematic diagram 500 is shown of an optical apparatus 501. As shown in FIG. 1, the optical apparatus 501 includes an optical component 502 that includes the self-arranging, luminescence-enhancement device 101 for surface-enhanced luminescence of FIG. 1. By way of example, in accordance with one embodiment of the present invention, an example configuration is shown for SERS, without limitation thereto, of molecules disposed between the metallic caps of the self-arranging, luminescence-enhancement device 101. In accordance with embodiments of the present invention, the self-arranging, luminescence-enhancement device 101 for surface-enhanced luminescence includes a substrate 110, and a plurality 120 of flexible columnar structures. In accordance with embodiments of the present invention, a flexible columnar structure 120-1 of the plurality 120 includes a flexible column 120-1A, and a metallic cap 120-1B coupled to the apex 120-1C of the flexible column 120-1A. In accordance with embodiments of the present invention, at least the flexible columnar structure 120-1 and a second flexible columnar structure 120-2 are configured to self-arrange into a close-packed configuration with at least one molecule 220-1 disposed between at least the metallic cap 120-1B and a second metallic cap 120-2B of respective flexible columnar structure 120-1 and second flexible columnar structure 120-2. Thus, previously described embodiments of the present invention for the self-arranging, luminescence-enhancement device 101 may be incorporated within the environments of the optical component 502 and the optical apparatus 501, without limitation thereto. Moreover, in accordance with embodiments of the present invention, the optical component 502 may be selected from the group consisting of a mirror, a grating, a wave-guide, and an analytical cell.

With further reference to FIG. 5, in accordance with embodiments of the present invention, the optical apparatus 501 may include a spectrometer, for example, a Raman spectrometer, without limitation thereto. FIG. 5 shows the configuration of the optical apparatus 501 including a spectrometer configured to accept the optical component 502 for performing spectroscopy, for example, SERS, of at least one molecule, for example, molecule 220-1, molecule 220-2, or molecule 410. The spectrometer includes a source of exciting electromagnetic radiation 510 that is used to excite at least one molecule, for example, molecule 410. The source of exciting electromagnetic radiation 510 may be a laser (not shown). The energy of a photon of the exciting electromagnetic radiation 510 is given by Planck's constant times the frequency of the laser source, given by: $H\nu_{laser}$. In addition, the spectrometer includes an analyzer (not shown) and a detector (not shown) that are used to analyze and detect emitted electromagnetic radiation 520. The scattered electromagnetic radiation 520 emerges from the molecule 410 in response to the exciting laser source. For example, in the case of SERS, the energy of a photon of the emitted electromagnetic radiation 520 from the molecule 410 is given by Planck's constant times the frequency of the molecular source, given by: $h\nu_{SERS} = h\nu_o \pm h\Delta$, □where $\nu_o$ is the frequency of the incident laser field and $\Delta$ the Raman shift. Because of the interaction with surface plasmons excited in the plurality of metallic caps, for example, metallic caps 120-1B and 120-2B, metallic caps 120-3B and 120-4B, and metallic caps 120-8B, 120-9B, 120-13B and 120-14B, of the plurality of flexible columnar structures, the magnitude of the local electric field $E_{molecule}$, at a molecule for example, molecule 220-1, molecule 220-2, or molecule 410, respectively, is enhanced compared to the incident field $E_o$.

With further reference to FIG. 5, in accordance with embodiments of the present invention, the composition of a metallic cap is such that the surface plasmons excited in the metallic cap are within the wavelength ranges of the exciting electromagnetic radiation 510 and the electromagnetic radiation emitted from the molecule 410; these wavelength ranges may extend from the near ultraviolet to the near infrared. Thus, in accordance with embodiments of the present invention, the plurality of metallic caps may be composed of a noble metal constituent; or alternatively, the plurality of metallic caps may be composed of a constituent selected from the group of constituents consisting of copper, silver and gold. In accordance with an embodiment of the present invention, the signal associated with the emitted electromagnetic radiation 520 is amplified by increasing the number of metallic caps in proximity to which a molecule is disposed. Embodiments of the present invention increase the number of metallic caps, for example, metallic caps 120-8B, 120-9B, 120-13B and 120-14B, in proximity to a molecule, for example, molecule 410, by employing a plurality 120 of flexible columnar structures including a plurality 610 (see FIG. 6B) of a flexible columns upon which the plurality 630 (see FIG. 6C) of metallic caps are disposed. Thus, in accordance with embodiments of the present invention, due to the increased number of metallic caps, an increase in the excitation of surface plasmnons in proximity to the molecule 410 is expected to enhance the signal from the molecule 410 in SERS. Therefore, embodiments of the present invention provide a self-arranging, luminescence-enhancement device 101 for surface-enhanced luminescence, for example, for SERS, without limitation thereto.

Figure 6A:
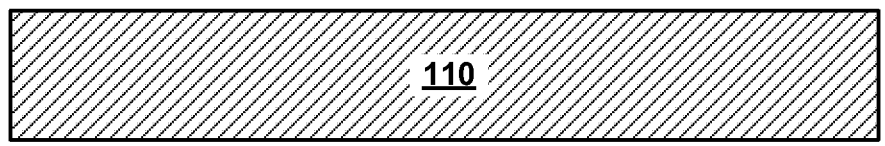
FIGS. 6A, 6B and 6C are cross-sectional elevation views at various stages in the fabrication of the self-arranging, luminescence-enhancement device of FIG. 1 illustrating a sequence of processing operations used in fabrication, in accordance with embodiments of the present invention.
Figure 6B:
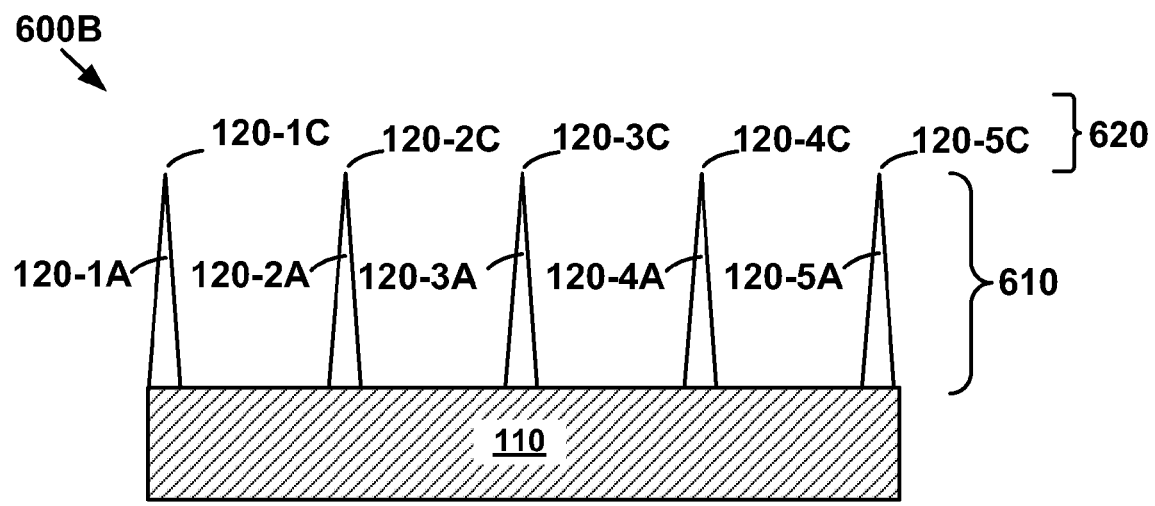
Figure 6C:
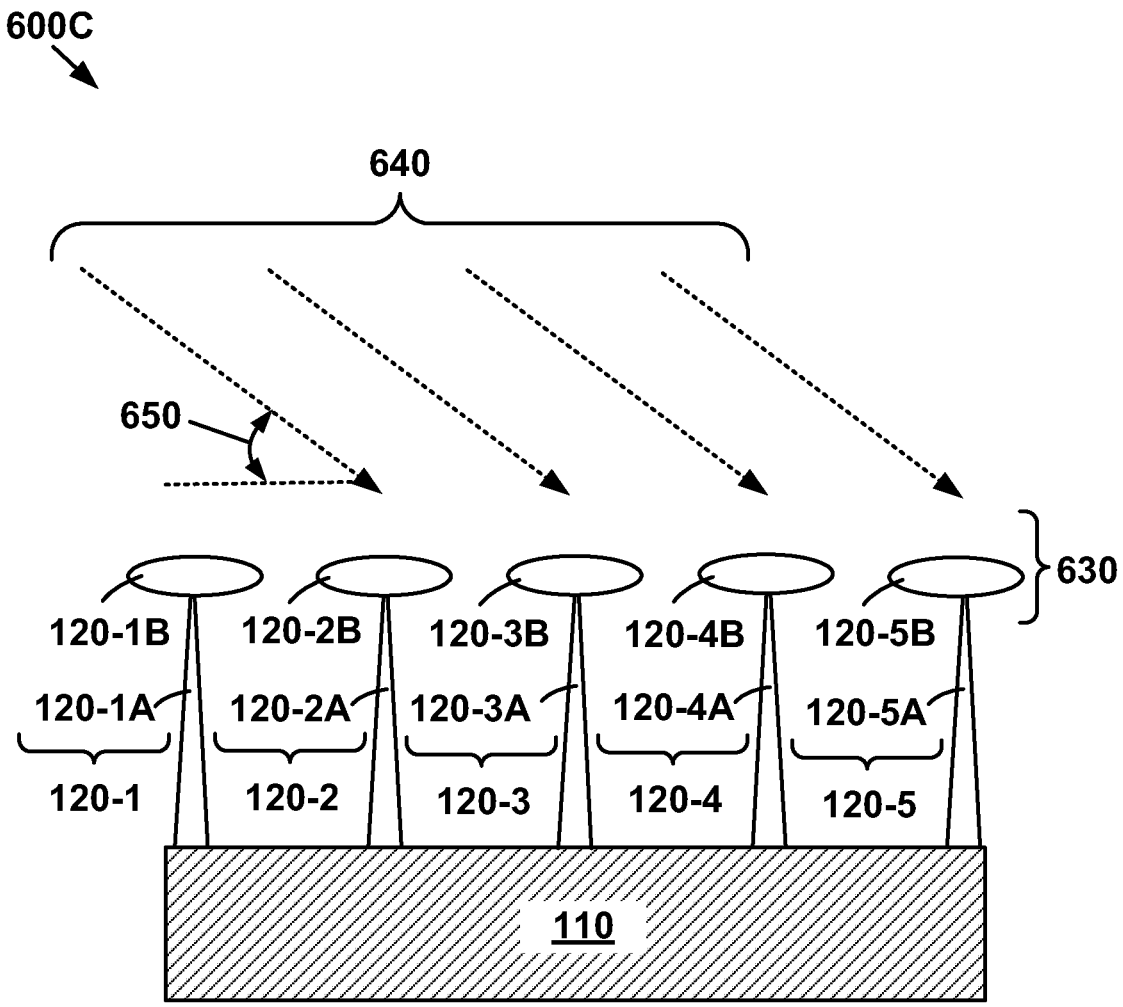

With reference now to FIGS. 6A, 6B and 6C, in accordance with yet other embodiments of the present invention, cross-sectional elevation views 600A, 600B and 600C, respectively, are shown of the self-arranging, luminescence-enhancement device 101 of FIG. 1 at various stages of fabrication of the self-arranging, luminescence-enhancement device 101. FIGS. 6A, 6B and 6C illustrate a sequence of processing operations used in fabrication of the self-arranging, luminescence-enhancement device 101. FIG. 6A shows a substrate 110 upon which the rest of the structure of the self-arranging, luminescence-enhancement device 101 is fabricated. In accordance with embodiments of the present invention, the substrate may be a material selected from the group consisting of silicon, glass, quartz, silicon nitride, sapphire, aluminum oxide, diamond, diamond-like carbon, one or more plastics, and one or more metals and metallic alloys. In accordance with embodiments of the present invention, the substrate may be in a form selected from the group consisting of a sheet, a wafer, a film and a web. For example, if the substrate is in the form of a web, the substrate may be used as feed stock, as rolls of material in a roll-to-roll fabrication process. For another example, the substrate may be in the form of a flexible polymer film composed of a plastic material, such as polyimide, polyethylene, polypropylene, or some other suitable polymeric plastic. Thus, in accordance with embodiments of the present invention, the substrate may be either rigid, as for a semiconductor wafer, or flexible, as for the web.

With further reference now to FIGS. 6B and 1, in accordance with embodiments of the present invention, a cross-sectional elevation view 600B is shown of the self-arranging, luminescence-enhancement device 101 of FIG. 1 at an intermediate stage of fabrication. FIG. 6B shows a plurality 610 of flexible columns, for example, flexible columns 120-1A, 120-2A, 120-3A, 120-4A and 120-5A, on the substrate 110. Each of the flexible columns of the plurality 610 of flexible columns, for example, flexible columns 120-1A, 120-2A, 120-3A, 120-4A and 120-5A, includes an apex of a plurality 620 of apices, for example, apices 120-1C, 120-2C, 120-3C, 120-4C and 120-5C. In accordance with embodiments of the present invention, the plurality 610 of flexible columns may be produced utilizing a process selected from the group consisting of growing nanowires on the substrate 110, etching the substrate 110, nano-imprinting a coating on the substrate 110, and hot nano-embossing a coating on the substrate 110. For example, in growing nanowires to produce the flexible columns, nanowire seeds are deposited onto the substrate 110, for example, silicon; and, the nanowire is grown during chemical vapor deposition from silane. By way of another example, in etching the substrate to produce the flexible columns, a reactive ion etching (RIE) process is applied to the substrate 110, for example, silicon; and, flexible columns, for example, in the form of nanocones, without limitation thereto, are produced by removing material from the substrate 110 through the action of reactive gaseous species, such as, fluorine, chlorine, bromine, or a halogen, in the presence of gaseous nitrogen, argon, or oxygen. By way of yet another example, in nanoimprinting the substrate to produce the flexible columns, a highly viscous thin film, for example, a highly cross-linked polymer, is applied to the substrate 110, for example, in the form of a web, to produce a coating on the web; and, flexible columns, for example, in the form of nanopoles, without limitation thereto, are produced by rolling the web between a pair of rolls, one of which is a die having a relief pattern that is impressed into the highly viscous thin film coating of the web leaving a negative of the relief pattern of the die in the form of a plurality of nanopoles on the web, substrate 110. By way of yet a further example, in hot nano-embossing a coating on the substrate 110, a polymer, or plastic, is applied to the substrate 110 to produce a coating on the substrate 110; and, flexible columns, for example, in the form of nanopoles, without limitation thereto, are produced by hot embossing the coating with a die, which has a relief pattern that is impressed into the polymer, or plastic, that coats the substrate 110 leaving a negative of the relief pattern of the die in the form of a plurality of nanopoles on the substrate 110.

With further reference now to FIGS. 6C and 1, in accordance with embodiments of the present invention, a cross-sectional elevation view 600C is shown of the self-arranging, luminescence-enhancement device 101 of FIG. 1 nearing a final stage in fabrication. HG. 6C shows a plurality 120 of flexible columnar structures, for example, flexible columnar structures 120-1, 120-2, 120-3, 120-4 and 120-5, on the substrate 110. Each of the flexible columnar structures, for example, flexible columnar structures 120-1, 120-2, 120-3, 120-4 and 120-5, includes a flexible column of the plurality 610 of flexible columns, for example, flexible columns 120-1A, 120-2A, 120-3A, 120-4A and 120-5A, and a metallic cap of a plurality 630 of metallic caps, for example, metallic caps 120-1B, 120-2B, 120-3B, 120-4B and 120-5B, such that each metallic cap is disposed upon an apex of the plurality 620 of apices, for example, apices 120-1C, 120-20, 120-30, 120-40 and 120-50, respectively. In accordance with embodiments of the present invention, the plurality 120 of flexible columnar structures may be produced utilizing a process selected from the group consisting of evaporating a metallic cap, for example, metallic cap 120-1 B, electroplating a metallic cap, precipitating a metallic cap from a colloidal suspension of metallic nanoparticles, lifting-off portions of a deposited metallic layer to form a metallic cap, and reducing adsorbed metalo-organic compounds by energetic particle bombardment to form a metallic cap.

For example, with further reference to FIGS. 6C and 1, in accordance with embodiments of the present invention, in evaporating to produce the metallic caps, a stream of metal vapor 640 is produced, using thin-film vacuum-evaporation techniques, to deposit metal onto the plurality 620 of apices of the plurality 610 of flexible columns 120-1A, 120-2A, 120-3A, 120-4A and 120-5A. The plurality 630 of metallic caps 120-1B, 120-2B, 120-3B, 120-4B and 120-53 are grown from the metal vapor depositing metal onto the plurality 620 of apices 120-1C, 120-2C, 120-3C, 120-4C and 120-5C of the plurality 610 of flexible columns 120-1A, 120-2A, 120-3A, 120-4A and 120-5A. In accordance with embodiments of the present invention, fabricating the plurality 630 of metallic caps may include evaporating metal at an angle 650 of about 30° to a surface of the substrate 110 onto a plurality 620 of apices 120-1 C, 120-2C, 120-3C, 120-4C and 120-5C of the plurality 610 of flexible columns 120-1A, 120-2A, 120-3A, 120-4A and 120-5A. Moreover, in accordance with embodiments of the present invention, the size, and consequently the spacing, of the metallic caps 120-1 B, 120-23, 120-3B, 120-43 and 120-53 can be controlled by limiting the amount of material deposited from the metallic vapor during the evaporation process.

By way of another example, with further reference to FIGS. 6C and 1, in accordance with embodiments of the present invention, in electroplating a metallic cap, the substrate 110 including the flexible columns 120-1A, 120-2A, 120-3A, 120-4A and 120-5A is immersed in a plating solution containing metal cations. An electrical potential is applied to the substrate 110 including the flexible columns 120-1A, 120-2A, 120-3A, 120-4A and 120-5A, which results in an enhanced electrical field at the apices, for example, apex 120-1C, of the flexible columns, for example, flexible column 120-1A. The enhanced electrical field attracts the metal cations to the apices, for example, apex 120-1C, of the flexible columns, for example, flexible column 120-1A, where chemical reduction of the metal cations occurs and metal is deposited to grow the metallic caps, for example, metallic cap 120-1B.

Similarly, by way of another example, with further reference to FIGS. 6C and 1, in accordance with embodiments of the present invention, in precipitating metallic caps from a colloidal suspension of metallic nanoparticles, the substrate 110 including the flexible columns 120-1A, 120-2A, 120-3A, 120-4A and 120-5A is immersed in a colloidal suspension of metallic nanoparticles; an electrical potential is applied to the substrate 110 including the flexible columns 120-1A, 120-2A, 120-3A, 120-4A and 120-5A, which results in an enhanced electrical field at the apices, for example, apex 120-1C, of the flexible columns, for example, flexible column 120-1A; the enhanced electrical field attracts metallic nanoparticles from the colloidal suspension to the apices, for example, apex 120-1 C, of the flexible columns, for example, flexible column 120-1A, where the metallic nanoparticles are deposited to grow the metallic caps, for example, metallic cap 120-1 B.

By way of yet another example, with further reference to FIGS. 6C and 1, in accordance with embodiments of the present invention, in a lift-off process for lifting-off portions of a deposited metallic layer to produce the metallic caps, a layer of photoresist is applied to the substrate 110 including the flexible columns 120-1A, 120-2A, 120-3A, 120-4A and 120-5A. An undercut structure is produced in the photoresist adjacent to the sides of the columns, and the photoresist is etched away from the apices 120-1 C, 120-2C, 120-3C, 120-4C and 120-5C of the flexible columns 120-1A, 120-2A, 120-3A, 120-4A and 120-5A. A stream of metal vapor 640 is deposited, using thin-film deposition techniques, for example, sputtering or evaporation, onto the plurality 620 of apices of the plurality 610 of flexible columns 120-1A, 120-2A, 120-3A, 120-4A and 120-5A. A thin film is deposited over the surface of the combined photoresist and partially fabricated self-arranging, luminescence-enhancement device 101. The photoresist and portions of the metal layer adhering to the photoresist between the flexible columns 120-1A, 120-2A, 120-3A, 120-4A and 120-5A is then removed and the plurality 630 of metallic caps 120-1 B, 120-2B, 120-3B, 120-4B and 120-5B is left adhering to the plurality 620 of apices 120-1C, 120-2C, 120-3C, 120-4C and 120-5C of the plurality 610 of flexible columns 120-1A, 120-2A, 120-3A, 120-4A and 120-5A.

By way of yet a further example, with further reference to FIGS. 60 and 1, in accordance with embodiments of the present invention, in reducing adsorbed metalo-organic compounds by energetic particle bombardment to produce the metallic caps 120-1B, 120-2B, 120-3B, 120-4B and 120-5B, the substrate 110 including the flexible columns 120-1A, 120-2A, 120-3A, 120-4A and 120-5A is exposed to a vapor of a chemical compound bearing a metal moiety, for example, a metalo-organic compound as used in chemical vapor deposition (CVD). For example, the metalo-organic compound may be provided in the form of a gas admitted to a vacuum chamber, such as, the vacuum chamber of a focused-ion beam (FIB) tool, a scanning electron microscope (SEM), or the target chamber of a laser ablation system, without limitation thereto. A suitable gas-injection system (GIS) interfaced to the vacuum chamber may be used to provide the chemical vapor bearing a metal moiety, for example, the metalo-organic compound. The gaseous vapor of the metalo-organic compound adsorbs on the surface of the substrate 110 including the apices 120-1C, 120-2C, 120-30, 120-40 and 120-50 of the flexible columns 120-1A, 120-2A, 120-3A, 120-4A and 120-5A. An energetic beam of particles, for example, ions, electrons, or photons, without limitation thereto, irradiates the apices 120-1C, 120-2C, 120-30, 120-4C and 120-50 of the flexible columns 120-1A, 120-2A, 120-3A, 120-4A and 120-5A. Such energetic beams of particles, for example, ions, electrons, or photons, without limitation thereto, may be provided, for example, by: the ion gun of a FIB tool, the electron gun of an SEM, or a laser of a laser ablation system, without limitation thereto. The energetic beam of particles, for example, ions, electrons, or photons, without limitation thereto, reduces the adsorbed gaseous vapor of the metalo-organic compound and grows the plurality 630 of metallic caps 120-1 B, 120-2B, 120-3B, 120-4B and 120-5B onto the plurality 620 of apices 120-1 C, 120-2C, 120-3C, 120-4C and 120-5C of the plurality 610 of flexible columns 120-1A, 120-2A, 120-3A, 120-4A and 120-5A.

Figure 7:
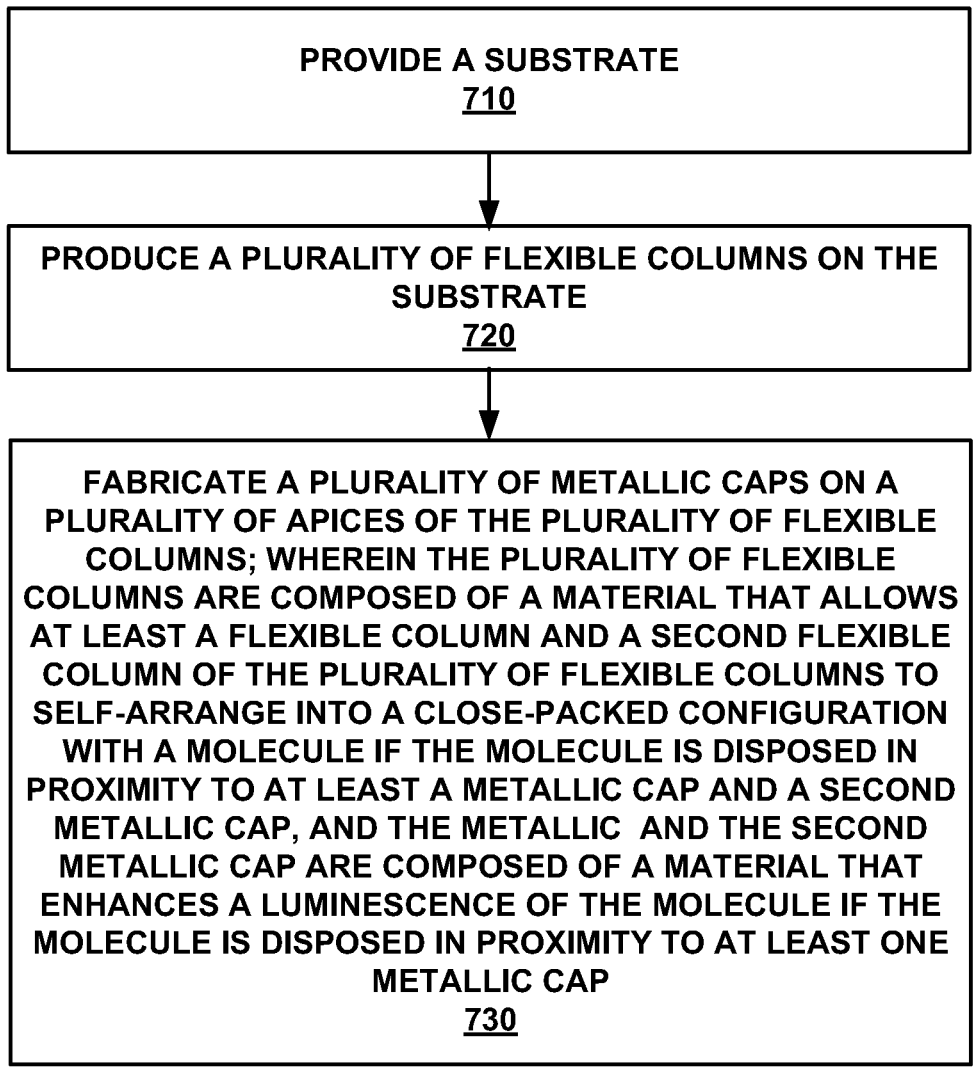
FIG. 7 is a flowchart of a method for fabricating a self-arranging, luminescence-enhancement device for surface-enhanced luminescence, in accordance with embodiments of the present invention.

With reference now to FIG. 7, in accordance with embodiments of the present invention, a flowchart 700 is shown of a method for fabricating a self-arranging, luminescence-enhancement device for surface-enhanced luminescence. The method for fabricating a self-arranging, luminescence-enhancement device for surface-enhanced luminescence includes the following. At 710, a substrate is provided. At 720, a plurality of flexible columns is produced on the substrate, In accordance with embodiments of the present invention, producing the plurality of flexible columns on the substrate may include a process selected from the group consisting of growing nanowires on the substrate, etching the substrate, hot nano-embossing a coating on said substrate, and nano-imprinting a coating on the substrate, as previously described. At 730, a plurality of metallic caps is fabricated on a plurality of apices of the plurality of flexible columns, such that the plurality of flexible columns are composed of a material that allows at least a flexible column and a second flexible column of the plurality of flexible columns to self-arrange into a close-packed configuration with a molecule if the molecule is disposed in proximity to at least a metallic cap and a second metallic cap, and the metallic cap and the second metallic cap are composed of a material that enhances a luminescence of the molecule if the molecule is disposed in proximity to at least one metallic cap. In addition, in accordance with embodiments of the present invention, fabricating the plurality of metallic caps may include a process selected from the group consisting of evaporating a metallic cap, electroplating a metallic cap, precipitating a metallic cap from a colloidal suspension of metallic nanoparticles, lifting-off portions of a deposited metallic layer to form a metallic cap, and reducing adsorbed metalo-organic compounds by energetic particle bombardment to form a metallic cap, as previously described. Moreover, in accordance with embodiments of the present invention, fabricating the plurality of metallic caps may also include evaporating metal at an angle of about 30° to the surface of the substrate onto the plurality of apices of the plurality of flexible columns, as previously described.

Embodiments of the present invention include a self-arranging, luminescence-enhancement device 101 that can provide enhanced sensitivity for the presence of molecules during surface-enhanced luminescence. Moreover, embodiments of the present invention provide for lower detectability omits for surface-enhanced luminescence of an analyte associated with a molecule in solution. For example, embodiments of the present invention provide for lower detectability limits in SERS analysis of a molecule. Thus, due to the enhanced sensitivity and detectability limits for molecular detection provided by embodiments of the present invention, the inventors expect new applications of embodiments of the present invention in at least medical, environmental, chemical, and biological technologies, without limitation thereto.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments described herein were chosen and described in order to best explain the principles of the invention and its practical application, to thereby enable others skilled in the art to best utilize the invention and various embodiments with various modifications as are suited to the particular use contemplated. It may be intended that the scope of the invention be defined by the claims appended hereto and their equivalents.

What is claimed is:

1. A self-arranging, luminescence-enhancement device for surface-enhanced luminescence, said device comprising:
    a substrate; and
    a plurality of flexible columnar structures, a flexible columnar structure of said plurality comprising:
        a flexible column; and
        a metallic cap coupled to an apex of said flexible column;
    wherein at least said flexible columnar structure and a second flexible columnar structure of said plurality of flexible columnar structures are configured to self-arrange into a close-packed configuration under influence of microcapillary forces between the flexible columnar structure and the second flexible columnar structure with at least one molecule disposed between at least said metallic cap and a second metallic cap of respective flexible columnar structure and second flexible columnar structure, and wherein said metallic cap of said flexible columnar structure and a metallic cap of said second flexible columnar structure are drawn laterally towards each other under the influence of microcapillary forces when in said close-packed configuration.

2. The self-arranging, luminescence-enhancement device of claim 1, wherein at least one metallic cap of said plurality of metallic caps is composed of a constituent selected from the group consisting of copper, silver, aluminum and gold, or any combination of copper, silver, aluminum and gold.

3. The self-arranging, luminescence-enhancement device of claim 1, wherein flexible columns of said plurality of flexible columnar structures further comprise a flexible material selected from the group consisting of a highly cross-linked uv-curable polymer, a highly cross-linked thermal-curable polymer, a highly cross-linked uv-curable plastic, a highly cross-linked thermal-curable plastic, a polysiloxane compound, silicon, silicon dioxide, silicon nitride, diamond, diamond-like carbon, spin-on glass, a sol-gel material, zinc oxide, aluminum oxide, sapphire, and titanium dioxide.

4. The self-arranging, luminescence-enhancement device of claim 1, wherein a metallic cap of said plurality of flexible columnar structures is configured to bind to a molecule disposed in close proximity to said metallic cap.

5. The self-arranging, luminescence-enhancement device of claim 1, wherein at least one flexible column is configured to bend towards at least a second flexible column, and to dispose said molecule in close proximity with at least a second metallic cap on said second flexible column.

6. The self-arranging, luminescence-enhancement device of claim 5, wherein a spacing of said close-packed configuration between said metallic cap and second metallic cap with a molecule disposed between said metallic cap and second metallic cap is determined by a balance of binding forces, between said molecule and said metallic cap and second metallic cap, with restoring forces exerted by said flexible column and second flexible column due to displacement of said flexible column and second flexible column towards said molecule.

7. The self-arranging, luminescence-enhancement device of claim 5, wherein said flexible column is configured to bend towards said second flexible column under action of microcapillary forces induced by removal of a fluid carrier provided to carry said molecule into proximity with said metallic cap and second metallic cap.

8. The self-arranging, luminescence-enhancement device of claim 1, wherein the flexible column of the flexible columnar structure and the flexible column of the second flexible columnar structure are spaced at the substrate by a gap of 20 nm to 500 nm.

9. The self-arranging, luminescence-enhancement device of claim 1, wherein the metallic cap of the flexible columnar structure and the metallic cap of the second flexible columnar structure, when self-arranged into the close-packed configuration, have a spacing of a size of an analyte molecule.

10. The self-arranging, luminescence-enhancement device of claim 1, wherein the columnar structure and the second columnar structure are bound in the close-packed configuration under influence of Van der Waals forces.

11. The self-arranging, luminescence-enhancement device of claim 1, wherein the self-arrangement of the first columnar structure and the second columnar structure is in absence of influence of an applied electric charge to either the first columnar structure or the second columnar structure.

12. A method for fabricating a self-arranging, luminescence-enhancement device for surface-enhanced luminescence, said method comprising:
    providing a substrate;
    producing a plurality of flexible columns on said substrate; and
    fabricating a plurality of metallic caps on a plurality of apices of said plurality of flexible columns;
    wherein said plurality of flexible columns are composed of a material that allows at least a flexible column and a second flexible column of said plurality of flexible columns to self-arrange into a close-packed configuration under influence of microcapillary forces between the flexible columnar structure and the second flexible columnar structure with a molecule if the molecule is disposed in proximity to at least a metallic cap and a second metallic cap, and said metallic cap and said second metallic cap are composed of a material that enhances a luminescence of said molecule if said molecule is disposed in proximity to at least one said metallic cap, and wherein said metallic cap and said second metallic cap are drawn laterally towards each other under the influence of microcapillary forces when in said close-packed configuration.

13. The method recited in claim 12, wherein said producing a plurality of flexible columns on said substrate comprises a process selected from the group consisting of growing nanowires on said substrate, etching said substrate, hot nano-embossing a coating on said substrate, and nano-imprinting a coating on said substrate.

14. The method recited in claim 12, wherein said fabricating said plurality of metallic caps comprises a process selected from the group consisting of evaporating a metallic cap, electroplating a metallic cap, precipitating a metallic cap from a colloidal suspension of metallic nanoparticles, lifting-off portions of a deposited metallic layer to form a metallic cap, and reducing adsorbed metalo-organic compounds by energetic particle bombardment to form a metallic cap.

15. The method of claim 12, wherein said fabricating said plurality of metallic caps comprises evaporating metal at an angle of about 30° to a surface of said substrate onto a plurality of apices of said plurality of flexible columns.

16. The method of claim 12, wherein the flexible column and the second flexible column are produced with a gap therebetween at the substrate of 20 nm to 500 nm.

17. An optical apparatus, comprising:
   an optical component comprising:
      a self-arranging, luminescence-enhancement device for surface-enhanced luminescence, said device comprising:
         a substrate; and
         a plurality of flexible columnar structures, a flexible columnar structure of said plurality comprising:
            a flexible column; and
            a metallic cap coupled to an apex of said flexible column;
         wherein at least said flexible columnar structure and a second flexible columnar structure of said plurality of flexible columnar structures are configured to self-arrange into a close-packed configuration under influence of microcapillary forces between the flexible columnar structure and the second flexible columnar structure with at least one molecule disposed between at least said metallic cap and a second metallic cap of respective flexible columnar structure and second flexible columnar structure, and to enhance luminescence from said molecule, and wherein said metallic cap and said second metallic cap are drawn laterally towards each other under the influence of microcapillary forces when in said close-packed configuration.

18. The optical apparatus of claim 17, said optical component is selected from the group consisting of a mirror, a grating, a wave-guide, and an analytical cell.

19. The optical apparatus of claim 17, further comprising:
   a spectrometer, said spectrometer configured to accept said optical component for performing surface-enhanced Raman spectroscopy of said molecule.

20. The optical apparatus of claim 17, wherein the flexible column of the flexible columnar structure and the flexible column of the second flexible columnar structure are spaced at the substrate by a gap of 20 nm to 500 nm.

* * * * *